United States Patent [19]
Harris

[11] Patent Number: 5,695,476
[45] Date of Patent: Dec. 9, 1997

[54] NEEDLE PROTECTION ASSEMBLIES

[76] Inventor: Ivan Paul Harris, 92 North Road, Great Clacton, Clacton-on-Sea, Essex CO15 4DE, United Kingdom

[21] Appl. No.: 640,803
[22] PCT Filed: Nov. 4, 1994
[86] PCT No.: PCT/GB94/02426
§ 371 Date: May 3, 1996
§ 102(e) Date: May 3, 1996
[87] PCT Pub. No.: WO95/13107
PCT Pub. Date: May 18, 1995

[30] Foreign Application Priority Data

Nov. 9, 1993 [GB] United Kingdom ............ 9323121

[51] Int. Cl.$^6$ .................................................. A61M 5/00
[52] U.S. Cl. ................................ 604/198; 604/192
[58] Field of Search ........................ 604/192, 198, 604/158–164

[56] References Cited

U.S. PATENT DOCUMENTS

| | | | |
|---|---|---|---|
| 4,957,488 | 9/1990 | Cameron et al. | 604/161 |
| 4,994,040 | 2/1991 | Cameron et al. | 604/160 |
| 5,395,347 | 3/1995 | Blecher et al. | 604/198 |
| 5,425,721 | 6/1995 | Malenchek | 604/198 |
| 5,496,274 | 3/1996 | Graves et al. | 604/192 |
| 5,498,244 | 3/1996 | Eck | 604/198 |
| 5,582,597 | 12/1996 | Brimhall et al. | 604/198 |
| 5,584,818 | 12/1996 | Morrison | 604/198 |

FOREIGN PATENT DOCUMENTS

| | | |
|---|---|---|
| 366336 | 5/1990 | European Pat. Off. . |
| 545671 | 6/1993 | European Pat. Off. . |

*Primary Examiner*—Gary Jackson
*Attorney, Agent, or Firm*—Pollock, Vande Sande & Priddy

[57] ABSTRACT

An intravenous needle protection assembly has a channel-shape housing with two rails along which a needle assembly and a guard can be slid. The needle assembly carries a cannula assembly that can be slid off the needle assembly at a forward position along the housing. A rearwardly-extending, inclined resilient tab projects from the bottom of the guard and engages a locking surface at the rear edge of a recess when the guard is in the forward position. When the needle assembly is subsequently slid back to a rear position, the guard covers the tip of the needle at the forward end of the housing. A forwardly-extending resilient tab on the needle assembly then engages a locking surface at the rear of the housing to lock the needle assembly in position.

9 Claims, 2 Drawing Sheets

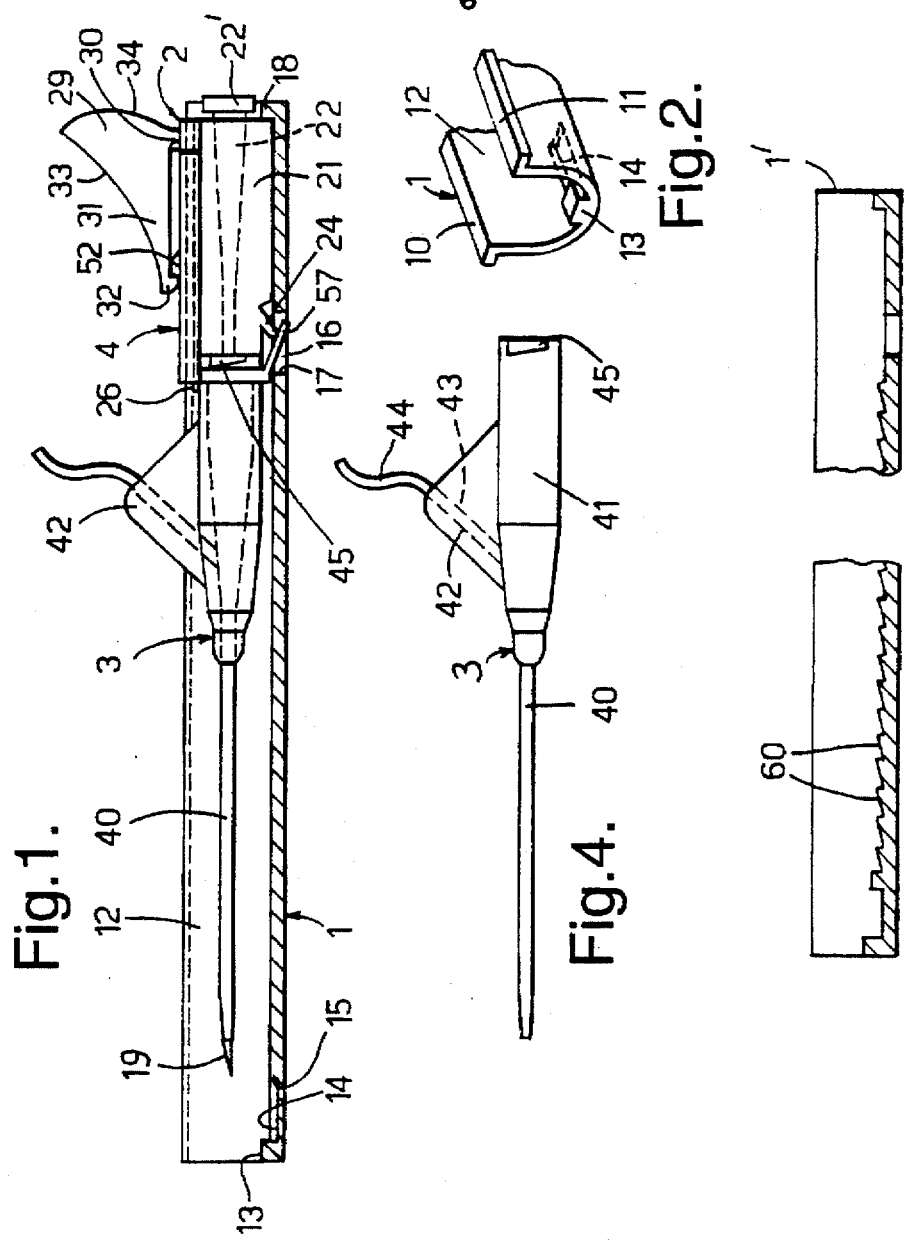

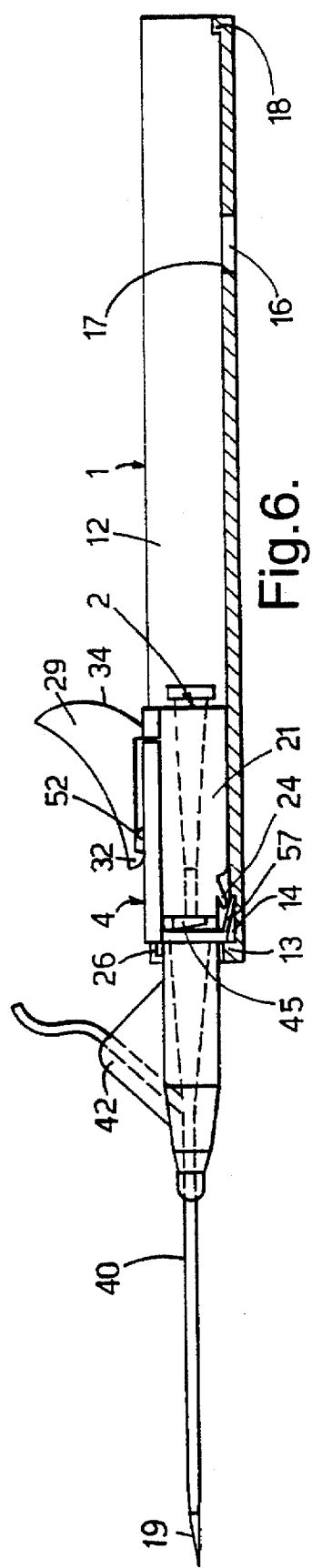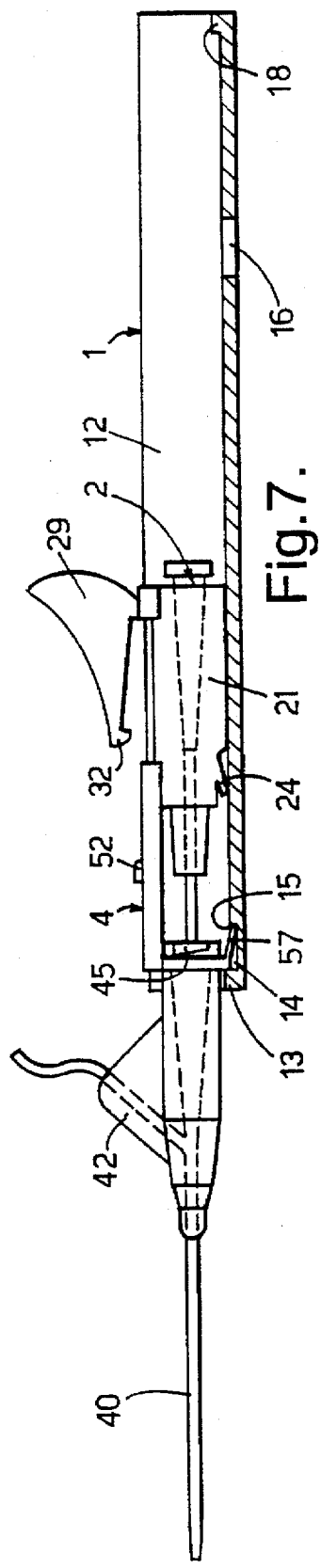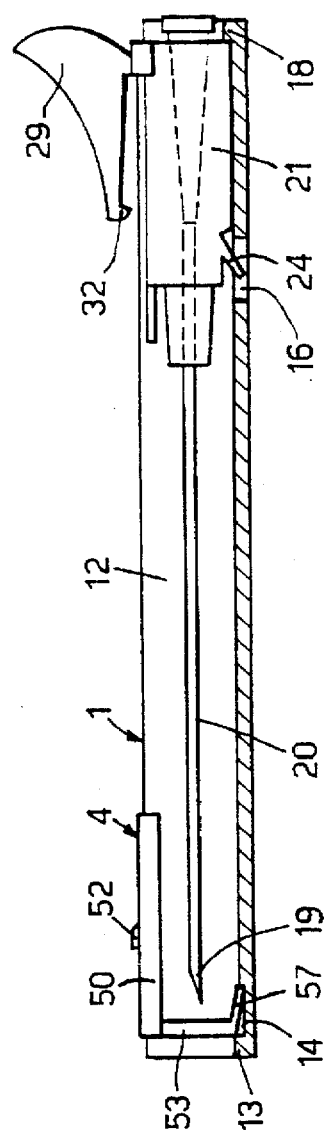

NEEDLE PROTECTION ASSEMBLIES

TECHNICAL FIELD

This invention relates to needle protection assemblies of the kind including a channel-shape protector housing having a slot opening along a major part of the length of the housing, a needle assembly slidable along the housing between a first position in which a tip of a needle is located within the housing and a second position in which the tip of the needle is exposed at one end of the housing and a cannula assembly mounted on the needle assembly such that it can be slid off the tip of the needle in the second position.

The invention is more particularly concerned with needle protection assemblies for intravenous cannula insertion devices, or the like.

BACKGROUND ART

Intravenous cannula insertion devices of the over-the-needle kind comprise a needle with a bevelled tip that projects by a short distance from the forward, patient end of an intravenous cannula. The cannula is inserted by pushing the needle tip into a vein, then sliding the cannula forwardly off the tip of the needle, into the vein, and withdrawing the needle from the rear end of the cannula. An example of such a device, including a tubular protector surrounding the device before use, is described in EP-A-0054671. The protector has a longitudinal slot along which the cannula hub is slid on insertion. After use, the needle is withdrawn into the protector, leaving the cannula in the vein. The protector provides protection from needle-stick injury before and after use. It is common practice, however, for some clinicians to bend the needle before use in order to give a preferred shape for introduction. In such a case, the tip of the needle can protrude from the slot of the protector when it is withdrawn after use. This can provide a hazard to the user.

DISCLOSURE OF THE INVENTION

It is an object of the present invention to provide an improved needle protection assembly.

According to the present invention there is provided a needle protection assembly of the above-specified kind, characterised in that the assembly includes a guard mounted on the needle assembly such that it is displaced forwardly to the one end of the housing when the needle assembly is slid to the second position, and a lock for retaining the guard at the one end of the housing when the needle assembly is retracted rearwardly to the first position, and that the guard covers the slot in the housing in the region of the tip of the needle when the needle assembly is retracted to the first position.

The lock preferably comprises a resilient catch on the guard and a locking surface on the housing. The resilient catch may be a rearwardly-extending inclined tab. The needle protection assembly preferably includes a second lock for locking the needle assembly in the first position after it has been retracted into the first position. The second lock may be provided by a forwardly-extending inclined tab on the needle assembly and a rearwardly-facing locking surface on the housing. When the guard is in the first position, the tab on the needle assembly may engage an upper surface of the tab on the guard so that when the needle assembly is slid forwardly, the tab on the guard deflects the tab on the needle assembly over the rearwardly-facing locking surface.

The guard preferably has a surface formation on an upper surface, the needle assembly having a surface formation at one end of an arm, the arm extending from a catch resiliently-mounted on the needle assembly, the needle assembly being displaced from the first to the second position by engaging one surface of the catch so that its arm is urged downwardly, and the needle assembly being displaced from the second to the first position by engaging another surface of the catch so that its arm is urged upwardly and the surface formation on the arm clears the surface formation on the guard. The guard may have a lateral plate with a non-circular aperture, the cannula assembly extending through the aperture and the rear end of the cannula assembly being shaped such that it can only pass through the aperture when oriented correctly. The housing may have a rail extending along its length, the needle assembly and guard both engaging the rail.

BRIEF DESCRIPTION OF DRAWINGS

An intravenous needle protection assembly in accordance with the present invention, will now be described, by way of example, with reference to the accompanying drawings, in which:

FIG. 1 is a partly sectional side elevation of the assembly in a first position;

FIG. 2 is an enlarged perspective view of a part of the housing of the assembly;

FIG. 3 is an enlarged perspective view of a part of the needle assembly;

FIG. 4 is an enlarged side elevation view of the cannula assembly;

FIG. 5 is an enlarged perspective view of the guard member;

FIG. 6 is a partly sectional side elevation of the needle protection assembly in a second position;

FIGS. 7 and 8 are partly sectional side elevation views of the needle protection assembly as the needle assembly is retracted to the first position; and FIG. 9 is a sectional side elevation of a modified housing for the assembly.

BEST MODES FOR CARRYING OUT THE INVENTION

With reference to FIGS. 1 to 5, the intravenous needle protection assembly comprises a protector housing 1 in which is mounted a needle assembly 2 supporting an intravenous cannula assembly 3 and a guard 4. The needle assembly 2 with the cannula assembly 3 and guard 4 are slidable along the housing 1.

The housing 1 is a U-shape channel of rigid plastics material with two longitudinal rails 10 and 11 projecting outwardly along opposite sides at the top of the housing. The top of the housing 1 is open along its length to provide a longitudinal slot 12. At the forward end of the housing a stop 13 projects upwardly from the floor of the housing to limit the extent of forward displacement of the needle assembly. Immediately to the rear of the stop 13, there is a shallow recess 14 with a vertical rear wall 15 that provides a first, forwardly-facing locking surface. The housing 1 also has an aperture 16 in its floor located a short distance forwardly of the rear end of the housing. The forward edge 17 of the aperture 16 provides a second, rearwardly-facing locking surface. A second stop 18 projects from the floor of the housing at the rear end, to limit rearward displacement of the needle assembly 2.

The needle assembly 2 comprises a hollow metal needle 20 with a bevelled tip 19 at its forward end and with a rear end moulded into a rigid plastics hub 21. The hub 21 is preferably transparent and is of generally cylindrical shape having a bore 22 communicating with the bore through the needle 20. The bore 22 is sealed at the rear end of the hub 21 by a hydrophobic filter 22', which allows venting of gas but prevents escape of blood. At its forward end, the hub has a tapered projection 23, which is makes a push fit in the rear of the cannula assembly 3. On the lower surface of the hub 21, just to the rear of the projection 23, there is a resilient locking catch 24 formed by a tab that inclines forwardly and downwardly. The upper surface 25 of the hub is flat and extends forwardly as a bar 26 over the rear part of the projection 23. At the rear end of the hub 21, a carriage 27 extends laterally on opposite sides of the hub above the top of the housing 1. The underside of the carriage 27 has a longitudinal recess 28 on each side in which the rails 10 and 11 are slidably received.

The hub 21 also includes an integral catch member 29 mounted on the carriage 27 by means of a resilient pillar 30. The catch member 29 has a forwardly-extending arm 31 with a downwardly-projecting inclined tooth 32 or similar surface formation at its forward end. The catch member 29 extends upwardly to form a forward, finger-engaging surface 33 of concave shape and a rear, finger-engaging surface 34 of convex shape.

With reference now especially to FIG. 4, the cannula assembly 3 is of conventional construction comprising a tubular plastics cannula 40 with a hub 41 at its rear end. A triangular wing 42 projects from the side of the hub 41 and encloses a branch bore 43 communicating between the bore through the cannula 40 and a flexible, small bore tube 44. The rear end of the hub 41 is open and has two bayonet locking lugs 45 projecting from its outer surface.

The final component of the needle-protection assembly is the guard 4 shown most clearly in FIG. 5. The guard 4 is a rigid plastics device with a flat horizontal plate 50 about 15 mm long, which extends above the top of the housing 1. The width of the plate 50 is slightly greater than that of the housing 1, the plate having longitudinal clips 51 underneath each opposite edge, which engage on respective ones of the rails 10 and 11. A short, laterally extending tooth 52 or similar surface formation projects from the upper surface of the plate 50 about half way along its length. The tooth 52 on the guard 4 is engaged by the tooth 32 on the catch 29 of the needle assembly 2 in the manner described later. At the forward end of the guard 4, there is a lateral, vertical plate 53 with a non-circular bayonet aperture 54. The aperture 54 has a central, circular region 55 and radially enlarged regions 56 above and below the circular region. The shape of the aperture 54 is such that the rear of the hub 41 on the cannula assembly 3 can be pushed through the aperture if the lugs 45 are aligned with the enlarged regions 56. Withdrawal of the hub 41 through the aperture 54 is prevented if the lugs 45 are out of alignment with the enlarged regions 56. A resilient locking catch formed by a tab 57 projects downwardly from the vertical plate 53 and is inclined rearwardly.

Industrial Applicability

Prior to use, the components of the needle protection assembly are assembled together in the manner shown in FIG. 1. The cannula assembly 3 is pushed fully onto the needle assembly 2 so that the tip 19 of the needle 20 projects from the forward end of the cannula 40. The guard 4 is locked onto the cannula assembly 3 with the lugs 45 to the rear of the vertical plate 53 and 90° out of alignment with the enlarged regions 56. The bar 26 on the needle hub 21 engages the sides of the lugs 45, between which it is located, and thereby prevents rotation of the cannula hub 41.

The wing 42 of the cannula assembly 3 projects vertically upwards out of the slot 12 of the housing 1. The horizontal plate 50 of the guard 5 extends rearwardly along the top of the needle hub 21 and is retained in position by engagement of the tooth 32 on the catch 29 with the forward edge of the tooth 52 on the guard 4. The catch 24 on the needle hub 21 contacts the upper surface of the catch 57 on the guard 4. Both the catches 24 and 57 project down into the aperture 16 so that the needle assembly 2 is retained at the rear end of the housing.

In this position, the guard 4 and cannula assembly 3 are securely retained on the needle assembly 2. The needle assembly 2 is retained at the rear end of the protector housing 1 with the tip 19 of the needle 20 protected within the housing and spaced from the end of the housing by about 1 cm. The catch 29 projects vertically out of the slot 12 of the housing 1 for access by the user.

The needle assembly 2, with the guard 4 and the cannula assembly 3 can be displaced forwardly to the position shown in FIG. 6 by pushing the rear, convex surface 34 of the catch 29. There is an initial resistance to forward movement of the needle assembly 1 because of engagement of the catches 24 and 57 in the aperture 16, which is sufficient to retain the assemblies in position until manual pressure is exerted. The rearwardly-inclined catch 57 on the guard 4 deflects the catch 24 on the needle assembly 1 upwardly so that it clears the forward locking edge 17 of aperture 16. When the guard 4 reaches the forward end of the housing 1, its catch 57 snaps down into the recess 14.

In the position shown in FIG. 6, the needle assembly 2 projects from the forward end of the housing so that the tip 19 of the needle 20 and the cannula 40 can be inserted in a vein in the usual way.

The user then withdraws the needle 20 by pushing against the concave, forward surface 33 of the catch 29. This rotates the catch in a clockwise sense about its pillar 30 so that the tooth 32 is lifted above the tooth 52 on the guard 4 and so that the needle assembly 2 can be slid rearwardly in the manner shown in FIG. 7. The guard 4, however, remains locked at the forward end of the housing 1 by engagement of its catch 57 against the rear edge 15 of the recess 14. The cannula assembly 3 can now be released from the housing 1 by twisting the housing through 90° so that the enlarged regions 56 in the aperture 54 of the guard 4 align with the lugs 45 on the cannula assembly 3.

When the needle assembly 2 is retracted rearwardly to its full extent, which is limited by engagement with the stop 18, the catch 24 on the needle assembly snaps into the aperture 16 so that subsequent forward displacement of the needle assembly is prevented by engagement of the catch with the forward edge 17. In this position, the tip 19 of the needle 20 is located beneath the horizontal plate 50 of the guard 4, about midway along its length so that access is prevented to the needle tip through the slot 12 in the housing 1. If the needle were bent upwardly, in its extended position, the tip 19 would still be retained below the guard 4 when retracted, in contrast with some previous needle protection assemblies.

In an alternative arrangement, as shown in FIG. 9, the floor of the housing 1' could have a series of rearwardly inclined ratchet teeth 60, which allow rearward displacement of the needle hub 21 but prevent forward displacement, at any position along the housing, by engagement of the catch 24 on the rear surfaces of the teeth.

It will be appreciated that the invention is not confined to intravenous needle assemblies.

I claim:

1. A needle protection assembly including a channel-shape protector housing having a slot opening along a major part of the length of the housing, a needle assembly slidable along the housing between a first position in which a tip of a needle is located within the housing and a second position in which the tip of the needle is exposed at one end of the housing, a cannula assembly mounted on the needle assembly such that it can be slid off the tip of the needle in the second position, characterised in that the assembly includes a guard mounted on the needle assembly such that it is displaced fowardly to the one end of the housing when the needle assembly is slid to the second position, and a lock for retaining the guard at the one end of the housing when the needle assembly is retracted rearwardly to the first position, and that the guard covers the slot in the housing in the region of the tip of the needle when the needle assembly is retracted to the first position.

2. An assembly according to claim 1, characterised in that the lock comprises a resilient catch on the guard and a locking surface on the housing.

3. An assembly according to claim 2, characterised in that the resilient catch is a rearwardly-extending inclined tab.

4. An assembly according to claim 1, wherein the needle protection assembly includes a second lock for locking the needle assembly in the first position after it has been retracted into the first position.

5. An assembly according to claim 4, characterised in that the second lock is provided by a forwardly-extending inclined tab on the needle assembly and a rearwardly-facing locking surface on the housing.

6. An assembly according to claim 5 wherein when the guard is in the first position the tab on the needle assembly engages an upper surface of the tab on the guard so that when the needle assembly is slid forwardly the tab on the guard deflects the tab on the needle assembly over the rearwardly-facing locking surface.

7. An assembly according to any one of the preceding claims, characterised in that the guard has a surface formation on an upper surface, that the needle assembly has a surface formation at one end of an arm, that the arm extends from a catch resiliently-mounted on the needle assembly, that the needle assembly is displaced from the first to the second position by engaging one surface of the catch so that its arm is urged downwardly, and that the needle assembly is displaced from the second to the first position by engaging another surface of the catch so that its arm is urged upwardly and the surface formation on the arm clears the surface formation on the guard.

8. An assembly according to any one of claims 1 to 6, wherein the guard has a lateral plate with a non-circular aperture, that the cannula assembly extends through the aperture, and that the rear end of the cannula assembly is shaped such that it can only pass through the aperture when oriented correctly.

9. An assembly according to any one of claims 1 to 6, wherein the housing has a rail extending along its length, and that the needle assembly and guard both engage the rail.

* * * * *